United States Patent
Platscher et al.

(10) Patent No.: US 10,000,445 B2
(45) Date of Patent: Jun. 19, 2018

(54) STABLE CRYSTAL MODIFICATIONS OF DOTAP CHLORIDE

(75) Inventors: Michael Wilhelm Platscher, Schlatt (CH); Alfred Hedinger, Thayngen (CH)

(73) Assignee: MERCK PATENT GMBH, Darmstadt (DE)

( * ) Notice: Subject to any disclaimer, the term of this patent is extended or adjusted under 35 U.S.C. 154(b) by 625 days.

(21) Appl. No.: 14/118,571

(22) PCT Filed: May 2, 2012

(86) PCT No.: PCT/EP2012/001882
§ 371 (c)(1),
(2), (4) Date: Nov. 19, 2013

(87) PCT Pub. No.: WO2012/159704
PCT Pub. Date: Nov. 29, 2012

(65) Prior Publication Data
US 2014/0093558 A1    Apr. 3, 2014

Related U.S. Application Data

(60) Provisional application No. 61/488,428, filed on May 20, 2011.

(51) Int. Cl.
| | | |
|---|---|---|
| A61K 31/20 | (2006.01) | |
| C07C 219/08 | (2006.01) | |
| A61K 31/231 | (2006.01) | |
| A61K 45/06 | (2006.01) | |

(52) U.S. Cl.
CPC .......... *C07C 219/08* (2013.01); *A61K 31/231* (2013.01); *A61K 45/06* (2013.01); *C07B 2200/07* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 5,264,618 A | 11/1993 | Felgner et al. | |
| 5,459,127 A | 10/1995 | Felgner et al. | |
| 5,925,623 A | 7/1999 | Nantz et al. | |
| 2003/0129223 A1 | 7/2003 | Wartchow et al. | |
| 2007/0049637 A1 | 3/2007 | De Ferra et al. | |
| 2008/0014254 A1 | 1/2008 | Platscher et al. | |

FOREIGN PATENT DOCUMENTS

| | | |
|---|---|---|
| DE | 4013632 A1 | 10/1991 |
| WO | 2005049549 A1 | 6/2005 |
| WO | 2006056312 A1 | 6/2006 |

OTHER PUBLICATIONS

Rodriguez-Spong et al. Adv. Drug Delivery Rev. 56 (2004) 241-274.*
International Search Report for PCT/EP2012/001882 dated Oct. 18, 2012.
Caira, M. R. et al., "Crystalline Polymorphism of Organic Compounds," Topics and Current Chemistry, 1998, vol. 198, pp. 163-208.
Pfohl, T. et al., "Biological polyelectrolyte complexes in solution and confined on patterned surfaces," Colloids and Surfaces A: Physicochemical and Engineering Aspects, 2002, vol. 198-200, pp. 613-623.
Perissi, I. et al., "Electron spin resonance and differential scanning calorimetry as combined tools for the study of liposomes in the presence of long chain nitroxides," J. Phys. Chem. B., 2002, vol. 106, pp. 10468-10473.
Kim, Y. J. et al., "Counterion Effects on Transfection Activity of Cationic Lipid Emulsion," Biotechnol. Bioprocess Eng., 2002, vol. 6, pp. 279-283.
Leventis, R. et al., "Interactions of mammalian cells with lipid dispersions containing novel metabolizable cationic amphiphiles," Biochimica et Biophysica Acta, 1990, vol. 1023, pp. 124-132.
Aberle, A. M. et al., "The Counterion influence on cationic lipid-mediated transfection of plasmid DNA," Biochimica et Biophysica Acta, 1996, vol. 1299, pp. 291-283.
Bennett, M. J. et al., "Cationic lipid-mediated gene delivery to murine lung: correlation of lipid hydration with in vivo transfection activity," J. Med. Chem., 1997, vol. 40, pp. 4069-4078.
Max Planck Gesellschaft, "Liposomes with positive excess charge," Espacenet, Publication Date: Oct. 31, 1991; English Abstract of DE-4013632.

* cited by examiner

*Primary Examiner* — Clinton A Brooks
*Assistant Examiner* — Ana Z Muresan
(74) *Attorney, Agent, or Firm* — Millen White Zelano and Branigan, PC; John Sopp

(57) ABSTRACT

The present invention relates to crystal modifications of racemic (2R,S)- and enantiomerically pure (2R)-resp. (2S)-DOTAP chloride, to processes for the preparation thereof, and to the use thereof for the preparation of pharmaceutical compositions.

15 Claims, 7 Drawing Sheets

STABLE CRYSTAL MODIFICATIONS OF DOTAP CHLORIDE

The present invention relates to crystal modifications of racemic and enantiomerically pure DOTAP chloride, to processes for the preparation thereof, and to the use thereof for the preparation of pharmaceutical compositions.

The crystalline forms of DOTAP chloride and corresponding pharmaceutical compositions have the same well-known uses as those of the non-crystalline forms of DOTAP chloride.

DOTAP chloride above and below denotes racemic (2R, S)- or isomerically pure (2R)-resp. (2S)-forms of N,N,N-trimethyl-2,3-bis[[(9Z)-1-oxo-9-octadecenyl]oxy]-1-propanaminium chloride, also known as (Z,Z)-N,N,N-trimethyl-2,3-bis[(1-oxo-9-octadecenyl)oxy]-1-propanaminium chloride or 1,2-dioleoyloxy-3-trimethylammonium propane chloride, and the hydrates thereof.

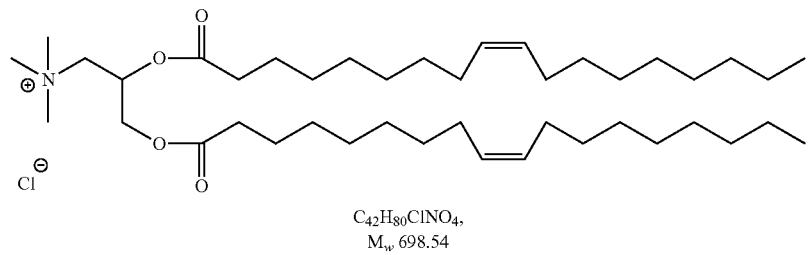 [SMILES: CCCCCCCC/C=C\CCCCCCCC(=O)OCC(C[N+](C)(C)C)OC(=O)CCCCCCC/C=C\CCCCCCCC ; [Cl-]]

$C_{42}H_{80}ClNO_4$,
$M_w$ 698.54

CAS numbers: 132172-61-3 and 477274-39-8 (racemate), 197974-73-58 (racemate, monohydrate) 428506-51-8 (2S form), 328250-28-8 (2R form)

DOTAP can amongst others build liposomes and other lipidic vesicular aggregates. Liposomes are synthetic multilayered vesicles (spherically self-contained membranes) comprising ambiphilic substances, usually natural lipids, into which both hydrophilic substances can be encapsulated into the aqueous interior, and also lipophilic substances can be incorporated into the inside of the lipid membrane.

They are employed in particular in cosmetics and in medicine, especially in dermatology. Here, in particular vitamins, coenzymes, skin-care agents and sunscreens are embedded. Liposomes are generally applied topically.

Additionally liposomes are increasingly achieving further importance in pharmaceutical technology, since parenteral application of liposomes enables more specific organ distribution to be achieved than if the active compounds are used in freely dissolved form.

If DNA, RNA or proteins are incorporated in liposomes and other lipidic vesicular aggregates, lipoplexes are obtained.

The addition of oils and the use of high-pressure homogenisers enable the formation of so-called nanoparticles (nanoparts) to be forced from liposomes. These are particles of approximately the same size as liposomes, but which do not have a water phase, but instead an oil phase in their interior. They are particularly suitable for the encapsulation of lipophilic substances.

Microemulsions are colloidally disperse, single-phase systems comprising aqueous, lipid-like and surfactant components. They have a particle size of 1-500 nm and behave in a similar manner to liquids.

Especially in connection with peptidic active compounds, nucleotides, vaccines and other biopharmaceuticals, which normally have poor solubility, the solubilising effect has very great importance in the case of the applications described above.

In addition, degradation of the active compounds in the body can be slowed and a sustained-release effect achieved in this way.

DOTAP chloride belongs to the class of cationic lipids. In contrast to naturally occurring phospholipids, these do not have a zwitterionic character. Liposomes comprising cationic lipids, alone or combined with phospholipids or other lipid-like compounds, have a positively charged surface. This gives rise to high affinity to cells which have a negatively charged surface on the outside, for example endothelial cells.

Particularly important, however, is the ability of DOTAP-based and other cationic liposomes and lipoplexes to penetrate into cells and thus to transport the active compounds incorporated therein into the interior of the cell (transfection).

All these properties make DOTAP chloride very interesting for cancer therapy too. These properties give rise to the possibility of applying conventional cytostatic agents incorporated in cationic DOTAP liposomes.

The transfection properties of DOTAP chloride and other DOTAP salts, such as, for example, the acetate, bromide, dihydrogenphosphate, hydrogensulfate, iodide, mesylate, methylsulfate, trifluoroacetate, sulfate or disulfate and triflate, are adequately known from the literature.

In some in-vitro studies, other salts, such as, for example, DOTAP methylsulfate, have achieved better transfection rates than DOTAP chloride.

Used in vivo, however, anion exchange at the liposome surface takes place in the living body, meaning that the advantages of other salts do not arise here. Especially on medical use in humans in particular for parenteral application, DOTAP salts with physiologically acceptable anions, such as, for example, the corresponding chloride or the acetate, are therefore preferred.

Medical, in particular parenteral applications make the highest demands of the quality and purity of the active compounds and adjuvants used. There are therefore very strict regulations on the part of the authorities with respect to the preparation, reproducibility of preparation and by-product profile of these compounds. In the case of substances used parenterally, microbiological contamination by pathogenic microorganisms and endotoxins must, in addition, be strictly avoided and controlled.

Currently available amorphous forms of DOTAP chloride and other DOTAP salts are extremely unstable and are therefore difficult per se to prepare in an acceptable purity so that they are suitable for use for the preparation of a medicament formulation.

Like all lipids which carry oleic acid radicals, such as, for example, the natural phospholipids DOPC and DOPE, all DOTAP salts are very sensitive to oxidation and the oxidation products of unsaturated fatty acid derivatives generally have high toxicity.

Suitable preparation, purification and stabilization methods are required here. DOTAP acetate, for example, is in the form of a high-boiling oil and industrially can therefore only be obtained with great difficulty in adequate quality.

Conventional methods of overcoming the instability, such as, for example, the addition of antioxidants in the form of ascorbic acid or reduced L-glutathione, greatly restrict the general usability of DOTAP chloride since interactions with the active compounds to be embedded later cannot be excluded. Complete exclusion of oxygen during the preparation, storage and use is virtually impossible or can only be facilitated with very great effort.

DOTAP chloride is commercially available as a chloroform solution or as an amorphous solid.

In addition to its oxidation sensitivity, amorphous DOTAP chloride is also extremely hygroscopic and deliquesces within an extremely short time at normal atmospheric humidity levels to give a greasy film. This makes handling of this compound much more difficult.

Technically any handling of currently available amorphous forms of DOTAP chloride is therefore only possible under vigorous protection measures. Thus, the manufacturer of amorphous DOTAP chloride generally recommends storage under protective gas at −20° C. and only guarantees a shelf life of about 6 months.

Eibel and Unger, DE4013632A1, outline the synthesis of (2R,S)-DOTAP chloride from DOTAP bromide by ion exchange in the chloroform/methanol/aqueous HCl solvent system followed by purification by means of chromatography. DOTAP bromide is obtained in advance in situ from 1-bromo-2,3-dioleoyloxypropane.

Leventis and Silvius, Biochim. Biophys. Acta, 1023 (1990) 124-132, report on the synthesis of (2R,S)-DOTAP chloride from DOTAP iodide by ion exchange in the two-phase solvent/NaCl solution system. DOTAP iodide is obtained in advance by methylation of the corresponding dimethylamino compound by means of methyl iodide.

Nantz et al., Biochim. Biophys. Acta, 1299 (1996) 281-283, J. Med. Chem. 40 (1997) 4069-4078, describe the synthesis of (2R,S)-DOTAP chloride by non-aqueous ion exchanger chromatography. The desired compound is obtained by evaporation of the eluate.

Feigner et al., U.S. Pat. No. 5,264,618, carry out the methylation of the corresponding dimethylamino compound directly to (2R,S)-DOTAP chloride by means of methyl chloride. They apparently obtain a yellow wax by crystallisation from acetonitrile at −20° C. However, (2R,S)-DOTAP chloride is virtually insoluble in acetonitrile at room temperature. Attempts to reproduce this so-called crystallisation gave only amorphous material through solidification of the oily substance obtained from hot solution on cooling. The fact that this is not a crystallisation is also evident from the fact that the authors apparently do not achieve a purification effect and have to purify the substance by chromatography. See also the comparative examples demonstrating that Feigner et al. does not achieve crystalline (2R,S)-DOTAP chloride.

In particular if the compounds are intended for parenteral use, a preparation which includes treatment with ion exchanger resin is extremely problematical in view of possible microbiological contamination, since corresponding resins are an ideal nutrient medium for bacteria and even after they have been killed, a risk of contamination by endotoxins still remains.

WO 2006/056312 A1 describes enantiomerically pure DOTAP chloride. A detailed process for crystallization is not disclosed.

The object of the present invention is therefore to provide crystalline DOTAP chloride salts and hydrates in high purity and with adequate chemical and physical stability. A further object of the present invention is to provide these crystalline salts with long shelf lives, enabling them to be used for the preparation of pharmaceutical formulations. There continues to be a great demand for a reproducible process for the preparation of stable forms of DOTAP chloride salts and hydrates which can be carried out on an industrial scale.

Enantiomerically pure DOTAP chloride can be obtained from enantiomerically pure starting materials analogously to the processes described for the racemate, i.e.

via (R)- or (S)-1-chloro-2,3-dioleoyloxypropane, via (R)- or (S)-1-LG-2,3-dioleoyloxypropane and ion exchange (LG=leaving group) or via (R)- or (S)-1-dimethylamino-2,3-dioleoyloxypropane. See WO 2006/056 312.

A further preparation method which may be mentioned is racemate resolution of racemic DOTAP chloride.

By means of experiments, it has now been found, surprisingly, that both racemic and also enantiomerically pure, crystalline DOTAP chloride can be obtained in a simple manner with high chemical purity, excellent stability and appropriate handling properties to handle these compounds on a larger technical scale. The crystalline products obtained in this way have virtually unlimited stability at room temperature under protective gas. They are therefore suitable as constituent or as starting material for the preparation of medicament forms.

The present invention accordingly relates to stable crystal modifications of racemic and enantiomerically pure DOTAP chloride.

The stable crystal modifications can be in crystalline and partially crystalline form. They have a never hitherto achieved purity of at least about 95%, preferably of >98%. Furthermore, (2R,S)-DOTAP chloride was found to have a never hitherto achieved stability of higher than 99% by weight and area-% determined by HPLC in relation to the starting value when stored at 25° C. for 36 months or at 40° C. for 12 months (see in this respect Table 1 and Table 1a).

A person skilled in the art can easily set-up a suitable HPLC method in order to determine the purity and content of DOTAP chloride. For example, an Agilent 1200 HPLC with an Inertsil ODS-3 column (150×3 mm, 3 μm) (GI Sciences) can be used as equipment. Typical eluents are 10 mM pentanesulfonic acid sodium salt in aqueous $H_3PO_4$ (0.085%) (eluent A) and 3.85 mM pentanesulfonic acid sodium salt in 94% acetonitrile containing aqueous $H_3PO_4$ (0.085%) (eluent B). A suitable gradient is the following (running time 25 min, post time 5 min; flow: 1.5 ml/min; 220 bar; 50° C., injection volume 10 μl):

|  | time | Eluent B | Eluent A |
| --- | --- | --- | --- |
| gradient | 0 min | 75% | 25% |
|  | 1 min | 75% | 25% |
|  | 6 min | 90% | 10% |
|  | 7 min | 100% | 0% |

-continued

|  | time | Eluent B | Eluent A |
|---|---|---|---|
|  | 20 min | 100% | 0% |
|  | 25 min | 75% | 25% |
| post time | 5 min | 75% | 25% |

The DOTAP chloride crystal modifications have a content of less than 1 equivalent of water or solvent of crystallisation per equivalent of DOTAP chloride.

Crystalline (2R)-, (2S)- and (2R,S)-DOTAP show excellent and highly desirable handling properties such as a remarkably reduced hygroscopicity and very good free-flowing capabilities.

Crystalline (2R)-, (2S)- and (2R,S)-DOTAP has a melting point above 160° C., particularly between 183 and 185° C., and a melting enthalpy of at least −130 J/g, preferably above −140J/g, particularly of between −143 and −159 J/g (see in this respect Table 3).

The racemic (2R,S)-DOTAP chloride crystal modifications exhibit moderately sharp bands in powder X-ray diffraction measurements (see in this respect FIG. 1 and Table 2).

2 Theta values for the crystal modification are approximately 6.5, 12.6, 13.4, 19.5, 20.2, 21.5, 25.2 and 29.8, wherein selected 2 theta values are approximately 12.6, 19.5, 20.2, 21.5 and 25.2. Crystalline forms of (2R,S)-DOTAP chloride corresponding to the X-ray powder diffraction pattern depicted in FIG. 1, are within the scope of the invention.

Enantiomerically pure (2S)-DOTAP chlorides are likewise obtained in crystalline form. 2 Theta values for the crystal modification are approximately 6.5, 12.8, 19.5, 19.8, 20.2, 20.7, 21.6 and 25.3, wherein selected 2 theta values are approximately 12.8, 19.5, 19.8, 20.2, and 21.6 (see FIG. 2 and Table 2). Crystalline forms of (2S)-DOTAP chloride corresponding to the X-ray powder diffraction pattern depicted in FIG. 2 are within the scope of the invention.

Enantiomerically pure (2R)-DOTAP chlorides are likewise obtained in crystalline form. 2 Theta values for the crystal modification are approximately 6.6, 12.8, 19.5, 19.8, 20.3, 20.8, 21.6 and 25.3, wherein selected 2 theta values are approximately 12.8, 19.5, 19.8, 20.3, and 21.6 (see FIG. 3 and Table 2). Crystalline forms of (2R)-DOTAP chloride corresponding to the X-ray powder diffraction pattern depicted in FIG. 3 are within the scope of the invention.

The invention furthermore relates to a process for the preparation of (2R)-, (2S)- and (2R,S)-DOTAP chloride crystal modifications which is characterised in that (2R)-, (2S)- and (2R,S)-DOTAP chloride is crystallised from an aprotic medium. The aprotic medium used for this purpose can be an aprotic solvent, or a mixture of aprotic solvents, or a mixture of one or more aprotic solvent with a protic solvent or a mixture of protic solvents.

Suitable aprotic solvents are aprotic, oxygen containing solvents, in particular, ethers, such as, for example, tetrahydrofuran, methyltetrahydrofuran, dioxane, diethyl ether, dipropyl ether, diisopropyl ether and methyl tert-butyl ether, ketones, such as, for example, acetone and 2-butanone, methyl isobutyl ketone, methyl isopropyl ketone, and esters, such as, for example, ethyl formate, methyl acetate, ethyl acetate, propyl acetate, isopropyl acetate, butyl acetate, isobutyl acetate, dimethyl carbonate, diethyl carbonate and 1,3-dioxolidin-2-one.

Preferred aprotic solvents are ketones.

Suitable protic solvents are, in particular, alcohols, such as, for example, methanol, ethanol, n-propanol, isopropanol, n-butanol, isobutanol, 2-butanol, tert-butanol, 3-methyl-1-butanol and ethylene glycol, methoxyethanol, ethoxyethanol.

If the aprotic medium is a mixture of one or more aprotic solvent with a protic solvent then the aprotic solvent may be an aprotic, oxygen containing solvent as defined above or a nitrile, such as, for example, acetonitrile.

The solvents may in each case be used in pure form or in the form of a mixture, i.e. it is possible both to use the various aprotic solvents in a group in the form of a mixture and also to employ aprotic solvent types in the form of a mixture with one another.

If the aprotic medium is a mixture of one or more aprotic solvent with a protic solvent then the protic solvents may be present from greater than 0% to 40% by weight, preferably from 10% to 20% by weight, depending on applied conditions, the purity of the raw materials and the target of the process (yield, purity of the product, degree of crystallinity). Preferably, an aprotic medium containing very low amounts of water should be employed. In an especially preferred embodiment water is excluded.

In a preferred embodiment of the invention acetone or 2-propanol are used as aprotic medium. In a very preferred embodiment a mixture of acetone and 2-propanol is employed. Typically, a mixture of 2-propanol and acetone comprises 0-25% of 2-propanol.

The crystallisation of the DOTAP chlorides can be carried out here directly from the reaction solution without prior purification. Likewise, crystalline DOTAP chloride can be obtained by recrystallization of amorphous, partially crystalline or crystalline material.

In a preferred embodiment, the DOTAP chlorides used for preparing crystalline forms thereof, are of high chemical and optical purity, preferably at a purity of about ≥95% or higher, more preferably about 98% or higher, even more preferably about 99% or higher. In this regard, the preparation of crystalline DOTAP chlorides herein use very pure oleic acid as a reactant, which leads to highly pure DOTAP chlorides that more easily crystallize than DOTAP chlorides available previously having less purity. Major impurities typical in DOTAP chlorides currently available include, but are not limited, to other lipids or derivatives thereof. The actual PhEUR purity (being therefore "pharma quality") of oleic acid is nowadays still only about 65-88%. By very pure oleic acid herein, it is meant an ultra-pure quality showing about 95% or higher, preferably about 99% or higher. A suitable very pure oleic acid can for example commercially obtained from RCA (lot OA 11.G.01.2007) or Acme Synthetic Chemicals (lot 060528).

The enantiomerical purity can for example be determined by determination of the optical rotation.

In a preferred embodiment, the DOTAP chlorides used for preparing crystalline forms thereof are crystallized or recrystallized out of mixtures with suitable solvents within concentration ranges from 1 part DOTAP chloride to 4 parts solvent up to1 part DOTAP chloride to 100 parts solvent, most preferably within concentration ranges from 1 part DOTAP chloride to 4 parts solvent up to1 part DOTAP chloride to 10 parts solvent.

The crystallisation of the DOTAP chloride modifications is generally achieved specifically by slow cooling of the prepared solution to temperatures below 30° C., for example, by cooling at a rate of 0.001° C. to 0.1° C. per minute, for example, 0.05° C. per minute or 0.004° C. per minute, leading to cooling times of about 5 to 200 hours, for example, about 10 hours to 50 hours. Specific options are to heat the solution to 35° C. and thereafter slowly cooling to −12° C. over a period of 12 hours, or to heat the solution to lower temperatures, e.g., 25° C., or start from room temperature without heating, and thereafter slowly cooling, e.g., from 10 to 50 hours, to preferably −12° C. The formation of the crystals is carried out either spontaneously or by inoculation with the corresponding DOTAP chloride crystal modification.

Slow cooling can be effectuated by any method known to a person skilled in the art. Typically, a cryostat is used.

As mentioned previously, all DOTAP salts are very sensitive to oxidation, and as such, the exclusion of oxygen during the preparation methods disclosed herein is preferred, e.g., by employing an inert atmosphere, e.g., nitrogen atmosphere and/or using solvents with a low oxygen and peroxide content.

The use of amorphous or partially crystalline DOTAP chloride as starting material for the recrystallization gives, by the process described, essentially crystalline DOTAP chlorides of never hitherto achieved purity together with never hitherto achieved stability.

The invention also relates to the use of crystalline (2R)-, (2S)- and (2R,S)-DOTAP chlorides for the preparation of medicament formulations since the crystalline (2R)-, (2S)- and (2R,S)-DOTAP chlorides have excellent stability in solid form under the stated conditions and have constant and very good quality for a virtually unlimited time.

The invention consequently furthermore also relates to the pharmaceutical compositions resulting from the use of the crystalline (2R)-, (2S)- and (2R,S)-DOTAP chloride forms claimed. Pharmaceutical compositions of this type can comprise the crystal modifications of (2R,S)-, (2S)- and (2R)-DOTAP chloride together with other pharmaceutical active compounds and known adjuvants usually employed in medicament preparation, as well as one or more solvents.

These pharmaceutical compositions can, for example, be in the form of liposomes, lipoplexes, microemulsions and nanoparticles and include, for example, an active compound from the group of the peptides, nucleotides, vaccines or cytostatic agents.

The present description enables the person skilled in the art to apply the invention in a comprehensive manner. In addition, the following examples serve for better understanding and for illustration of possible variants of the invention. These examples should therefore in no way be regarded as restrictive.

All temperatures mentioned in the following examples are indicated in degrees Celsius. Unless stated otherwise, content data are given as % by weight.

EXAMPLES FOR ILLUSTRATING THE INVENTION

Figure 1:
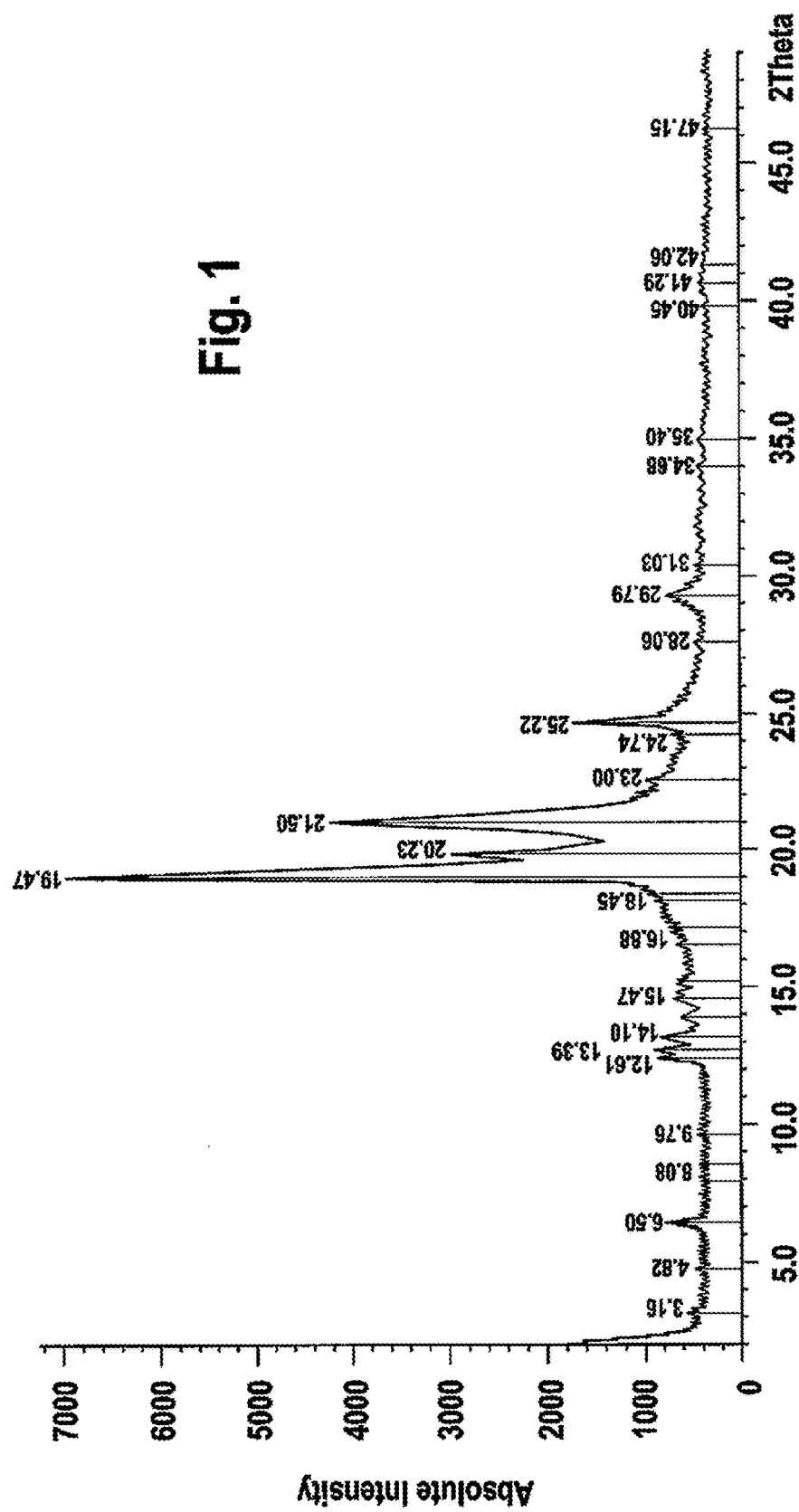
FIG. 1 illustrates x-ray spectra for crystalline (2R,S)-DOTAP chloride.

General Remarks About Experimental Conditions:

It is important to cool down very slowly during crystallization and recrystallization in order to optimize precipitation of crystalline material.

All reagents and solvents comprise very low water contents.

All operations are carried out in closed equipment under nitrogen atmosphere.

Very pure oleic acid having a purity of more than 95%, preferably more than 98%, even more preferably more than 99% is used.

Measurement Parameters for the X-Ray Powder Diffraction are as Follows:
STOE X-Ray Powder Diffraction
Diffraction: Transmission
Monochromator: Curved Germanium (111)
Radiation Wavelength: 1.54060 Cu
Detector: Linear Position Sensitive Detector
Scan Mode: Debye-Scherrer/Moving Position Sensitive Detector/Fixed Omega It is common in X-ray powder diffraction studies that slight differences of individual bands may occur if different instruments or recording methods, such as reflection or transmission, or capillary or window, are utilized, or if different recording conditions (e.g., atmospheric humidity or temperature) prevail. One of ordinary skill in the art is very familiar with such slight differences and would readily be capable of identifying a given material by a close match to a given X-ray powder diffraction pattern in consideration of the methodology used.

Preparation Example 1

Preparation of crystalline racemic (2R,S)-DOTAP Chloride[(R,S)-1,2-dioleoyl-3-propyltrimethylammonium chloride]

Starting Materials
The following chemicals were used:
N,N'-carbonyldiimidazole from SIGMA-ALDRICH, lot 1252812 Oleic acid from RCA, lot OA 11.G.01.2007, 99.1 Area-% (HPLC), where the assay might be 99.5% or even higher as linoleic acid (the major impurity) shows much higher response rates in UV than oleic acid.
(R,S)-3-(dimethylamino)-1,2-propanediol, from MERCK EPROVA, lot MSCH-103-A,
0.11% water, 99.4% (GC)
1,8-Diazabicyclo[5.4.0] undec-7-ene from SIGMA ALDRICH, lot 1076841, 99.7% (GC)
Methyl chloride from LINDE, lot 61448
Sodium iodide from SIGMA-ALDRICH, lot 1336385, 0.27% water Aluminium oxide from SIGMA-ALDRICH, lot 1336643
Acetonitrile from ICC, lot 0000426130, 100.0% (GC), <0.015% water n-Heptane from BRENNTAG SCHWEIZERHALL, lot 0000278245, 96.4% (GC)
2-Propanol from THOMMEN FURLER, lot 070920211487, 99.96% (GC), 0.03% water
Acetone from THOMMEN FURLER, lot 080609324212, 99.98% (GC), 0.16% water Synthesis of (2R,S)-DODAP [(R,S)-1,2-dioleoyl-3-dimethylammonium propane]

2.41 kg of N,N'-carbonyldiimidazole is dissolved at room temperature in 6.33 kg of dry acetonitrile. The resultant solution is heated to 25° C. Then 4.0 kg of oleic acid is pumped into the solution over a period of 60 minutes while the reaction temperature is regulated below 35° C. by the variation of the addition speed (formation of carbon dioxide gas). After the addition is completed the reaction solution is stirred for additional 90 minutes at 30° C. (gas evolution ended). Then 11 g of 1,8-diazabicyclo[5.4.0]undec-7-ene is added followed by a solution of 0.83 kg of racemic (R,S)-3-(dimethylamino)-1,2-propanediol in 0.37 kg of dry acetonitrile. Stirring at 30° C. is continued for 21 hours. The resultant emulsion is cooled to 25° C. and stirring is stopped. Two layers appear. The lower layer is isolated, degassed at 1 mbar/25° C. for 200 minutes and finally diluted with 11.7 kg n-heptane. To the solution is added 1.21 kg of basic aluminium oxide and the suspension is stirred for 3 hours at 0° C. The suspension is filtered and the filter residue is washed with 1.5 kg of n-heptane previously cooled down to 0° C. The combined filtrates are homogenized to yield 15.9 kg solution of 4.08 kg pure (2R,S)-DODAP in n-heptane (lot no. MBA-116, assay: 25.7%, yield: 88.9%).

Another batch is carried out the same way resulting in 16.6 kg solution of 3.52 kg pure (2R,S)-DODAP in n-heptane (lot no. MBA-117, assay: 21.2%, yield: 88.6%).

Synthesis of (2R,S)-DOTAP Chloride 23.4 kg solution of 3.52 kg pure (2R,S)-DODAP in n-heptane (15.9 kg of lot no. MBA-116 and 7.5 kg of lot no. MBA-117) is charged into the reaction vessel and the n-heptane is distilled off at a jacket temperature of 60° C. and reduced pressure. When the vacuum remains stable at 8 mbar the jacket temperature is adjusted to 25° C. Then 7.0 kg of 2-propanol is added followed by 3.1 g of sodium iodide. Then the reaction temperature is adjusted to 30° C. and the nitrogen atmosphere is replaced by a methyl chloride atmosphere with constant absolute pressure of 1200 mbar. The reaction mixture is stirred under these conditions for 137 hours until the methylation reaction of (2R,S)-DODAP to (2R,S)-DOTAP Chloride is finished (96% conversion). The consumption of methyl chloride is 1.39 kg.

Crystallization of (2R,S)-DOTAP Chloride

The solution of (2R,S)-DOTAP Chloride in 2-propanol prepared as described above is diluted with 35.8 kg dry acetone at 25° C. The amount of 2-propanol, as noted above, is 7 kg and the amount of DOTAP chloride based on calculations is 3.64 kg in the solution. The clear solution is slowly cooled down to −12° C. with a cooling rate of 0.05° C. per minute, i.e., the cooling down occurs over a time period of 12⅓ hours. The resultant suspension is kept at −12° C. for an additional 14 hours and is then filtered through a precooled filter (−15° C.). The crude (2R,S)-DOTAP Chloride is washed twice with 6.0 kg of cold dry acetone (−18° C.).

The obtained crystal modification at this point in this particular experiment is not checked; however, from earlier corresponding experiments in which the raw product was isolated at this point, it is known that the crystal modification is that of crystalline (2R,S)-DOTAP.

To achieve an even purer product, i.e., to remove some minor impurities, a recrystallization step is performed.

Recrystallization of (2R,S)-DOTAP Chloride

The wet crude (2R,S)-DOTAP Chloride is dissolved in the closed filter in a mixture of 44.1 kg of dry acetone and 3.5 kg 2-propanol at 35° C. The solution is transferred to the reaction vessel and brought to 0° C. The solution is slowly cooled down to −12° C. with a cooling rate of 0.004° C. per minute, i.e., the cooling down occurs over a time period of 50 hours. The resulting suspension is kept at −12° C. for additional 16 hours and is then filtered with a cooled filter-dryer (−15° C.). The filter residue is washed twice with 0.8 kg of cold dry acetone (−18° C.) and dried by applying vacuum. During drying the filter-dryer is allowed to warm up to room temperature. The drying is complete when the vacuum is stable at 7.9 mbar. Yield: 3.46 kg crystalline racemic (2R,S)-DOTAP chloride (crystalline (2R,S)-DOTAP, lot no. MBA-118, assay: 100.0%, yield: 37.8% ref. to (R,S)-3-(dimethylamino)-1,2-propanediol, HPLC purity: 99.9% area).

Preparation Example 2

Preparation of crystalline enantiomerically pure (2R)-DOTAP Chloride [(R)-1,2-dioleoyl-3-propyltrimethylammonium chloride]

Starting Materials
The following chemicals were used:
N,N'-carbonyldiimidazole from SIGMA-ALDRICH, lot 1252812 Oleic acid from ACME SYNTHETIC CHEMICALS, lot 060528, 97.8% (HPLC)
(R)-3-(dimethylamino)-1,2-propanediol, from DAISO, lot RMA062151, 0.11% water, 99.6% (GC)
1,8-Diazabicyclo[5.4.0]undec-7-ene from SIGMA ALDRICH, lot 1076841, 99.7% (GC)
Methyl chloride from LINDE, lot 61448
Sodium iodide from SIGMA-ALDRICH, lot 1336385, 0.27% water
Acetonitrile from SIGMA ALDRICH, lot 7219K, 100.0% (GC), 0.005% water n-Heptane from BRENNTAG SCHWEIZERHALL, lot 0000278245, 96.4% (GC)
2-Propanol from THOMMEN FURLER, lot 070629176434, 99.96% (GC), 0.016% water
Acetone from THOMMEN FURLER, lot 061201101946, 99.98% (GC), 0.10% water Synthesis of (2R)-DODAP [(R)-1,2-dioleoyl-3-dimethylammonium propane]

1.63 kg N,N'-carbonyldiimidazole is dissolved at room temperature in 4.3 kg of dry acetonitrile. The solution is heated to 25° C. Then 2.7 kg of oleic acid is pumped into the solution over a period of 60 minutes while the reaction temperature is regulated below 35° C. by the variation of the addition speed (formation of carbon dioxide gas). After the addition is completed the reaction solution is stirred for additional 105 minutes at 30° C. (gas evolution ended). Then 7.5 g of 1,8-diazabicyclo[5.4.0]undec-7-ene is added followed by a solution of 0.56 kg of enantiomerically pure (R)-3-(dimethylamino)-1,2-propanediol in 0.25 kg dry acetonitrile. Stirring at 30° C. is continued for 19 hours. The resultant emulsion is cooled to 10° C. and stirring is stopped. Two layers appear. The lower layer is isolated, degassed at 0.1 mbar/20° C. for 30 minutes and finally diluted with 9.7 kg of n-heptane. The suspension is stirred for 1.5 hours at 0°

C. and filtered to yield 12.3 kg solution of 2.66 kg pure (2R)-DODAP in n-heptane (lot no. MBR-001, assay: 21.6%, yield: 88.4%).

Synthesis of (2R)-DOTAP Chloride 12.2 kg solution of 2.66 kg pure (2R)-DODAP in n-heptane (lot no. MBR-001) is charged into the reaction vessel and the n-heptane is distilled off at a jacket temperature of 60° C. and reduced pressure. When the vacuum remains stable at 1 mbar, the jacket temperature is adjusted to 20° C. Then 3.26 kg of 2-propanol is added followed by 1.4 g sodium iodide. Then the reaction temperature is adjusted to 30° C. and the nitrogen atmosphere is replaced by a methyl chloride atmosphere with constant absolute pressure of 1250 mbar. The reaction mixture is stirred under these conditions for 330 hours until the methylation reaction of (2R)-DODAP to (2R)-DOTAP Chloride is finished (97% conversion). The consumption of methyl chloride is 0.58 kg.

Crystallization of (2R)-DOTAP Chloride

The solution of (2R)-DOTAP Chloride in 2-propanol prepared as described above is diluted with 16.2 kg dry acetone at 25° C. The amount of 2-propanol, as noted above, is 3.26 kg and the amount of DOTAP chloride based on calculations is 2.78 kg in the solution. The clear solution is slowly cooled down to −12° C. with a cooling rate of 0.05° C. per minute, i.e., the cooling down occurred over a time period of 12⅓ hours. The resulting suspension is kept at −12° C. for an additional hour and is then filtered through a precooled filter (−12° C.). The crude (2R)-DOTAP Chloride is washed twice with 3.2 kg of cold dry acetone (−18° C.). The crystalline product is that of crystalline (2R)-DOTAP.

The obtained crystal modification at this point in this particular experiment is not checked; however, from earlier corresponding experiments in which the raw product was isolated at this point, it is known that the crystal modification is that of crystalline (2R)-DOTAP.

To achieve an even purer product, i.e., to remove some minor impurities, a recrystallization step is performed.

Recrystallization of (2R)-DOTAP Chloride

The wet crude (2R)-DOTAP Chloride is dissolved in the closed filter in a mixture of 20.5 kg dry acetone and 1.63 kg of 2-propanol at 35° C. The solution is transferred to the reaction vessel and brought to 25° C. The solution is slowly cooled down to −12° C. with a cooling rate of 0.05° C. per minute, i.e., the cooling down occurs over a time period of 12⅓ hours. The resulting suspension is kept at −12° C. for additional 9 hours and is then filtered with a cooled filter-dryer (−12° C.). The filter residue is washed twice with 3.2 kg of cold dry acetone (−18° C.) and dried by applying vacuum. During drying the filter-dryer is allowed to warm up to room temperature. The drying is complete when the vacuum is stable at 0.6 mbar. Yield: 1.47 kg crystalline enantiomerically pure (2R)-DOTAP chloride (lot no. MBR-002, assay: 99.7%, yield: 44.7% ref. to (R)-3-(dimethylamino)-1,2-propanediol, HPLC purity: 99.9% area).

Preparation Example 3

Preparation of crystalline enantiomerically pure (2S)-DOTAP Chloride [(S)-1,2-dioleoyl-3-propyltrimethylammonium chloride]

(2S)-DOTAP Chloride [(S)-1,2-dioleoyl-3-propyltrimethylammonium chloride] is manufactured in the same way as (R)-DOTAP Chloride (see above) just by starting from the enantiomerically pure starting material (S)-3-(dimethylamino)-1,2-propanediol (lot SMA062281 from DAISO, 0.14% water, GC: 99.8%; all other chemicals are identical) and yields 1.67 kg crystalline enantiomerically pure (2S)-DOTAP Chloride (lot no. MBS-002, assay: 99.6%, yield: 50.4% ref. to (S)-3-(dimethylamino)-1,2-propanediol, HPLC purity: 100.0% area).

Characterization Example 1

Stabilities

In order to determine the stability of crystalline (2R,S)-DOTAP chloride, the substance is stored at 25° C. and 60% relative humidity (table 1) or at 40° C. and 75% relative humidity (table 1a) with exclusion of air. The remaining content of (2R,S)-DOTAP chloride is measured at periodic intervals and quoted in comparison to the initial value.

The purity and content of DOTAP chloride are determined by means of HPLC using the following method:
HPLC equipment: Agilent 1200 HPLC
column: ODS-3: 150×3 mm, 3 µm. GI Sciences: lnertsil
eluent A: 10 mM pentanesulfonic acid sodium salt in 0.085%ic aqueous $H_3PO_4$
eluent B: 3.85 mM pentanesulfonic acid sodium salt in 94% acetonitrile containing 0.085%ic aqueous $H_3PO_4$

| gradient: | 0 min | 75% B |
|---|---|---|
| | 1 min | 75% B |
| | 6 min | 90% B |
| | 7 min | 100% B |
| | 20 min | 100% B |
| | 25 min | 75% B |
| posttime: | 5 min | 75% B | runtime: 25 min
flow: 1.5 ml/min
pressure: ca. 220 bar
column temperature: 50° C.
injection volume: 10 µl The following values are found:

The stability determination can be repeated at any desired time, the values indicated in Tables 1 and 1a are reproducible.

TABLE 1

Storage conditions: 25° C.

| (2R,S)-DOTAP chloride crystalline | Exposure time in months | | | | | | |
|---|---|---|---|---|---|---|---|
| | 0 | 3 | 6 | 9 | 12 | 24 | 36 |
| Area-% | 99.7 | 99.6 | 99.5 | 99.2 | 99.5 | 99.7 | 99.3 |
| % by weight | 99.5 | 99.7 | 99.4 | 99.2 | 99.5 | 99.5 | 99.7 |

The above stability data confirms that crystalline DOTAP chloride is a stable substance. Even after 36-months no significant degradation was observed for the samples stored at 25 ± 2° C.

TABLE 1a

Storage conditions: 40° C.

| (2R,S)-DOTAP chloride crystalline | Exposure time in months | | | | |
|---|---|---|---|---|---|
| | 0 | 3 | 6 | 9 | 12 |
| Area-% | 99.7 | 99.6 | 99.4 | 99.3 | 99.4 |
| % by weight | 99.5 | 99.6 | 99.6 | 98.9 | 99.7 |

The above stability data confirms that crystalline DOTAP Chloride is a stable substance. Even at accelerated conditions after 12-months no significant degradation was observed for the samples stored at 40 ± 2° C.
Crystalline (2R)- and (2S)-DOTAP chloride show comparable stability values.

Characterization Example 2

Powder X-Ray Diagrams

For characterisation of the structural properties (crystal modifications) of crystalline DOTAP chlorides, powder X-ray diagrams (diffraction spectra) of these substances are recorded.

Crystalline (2R,S)-, (2R)- and (2S)-DOTAP chlorides give spectra with moderately sharp bands which have relatively good resolution for lipids. The spectra indicate high crystalline contents. No amorphous fractions are visible under the polarising microscope.

Figure 2:
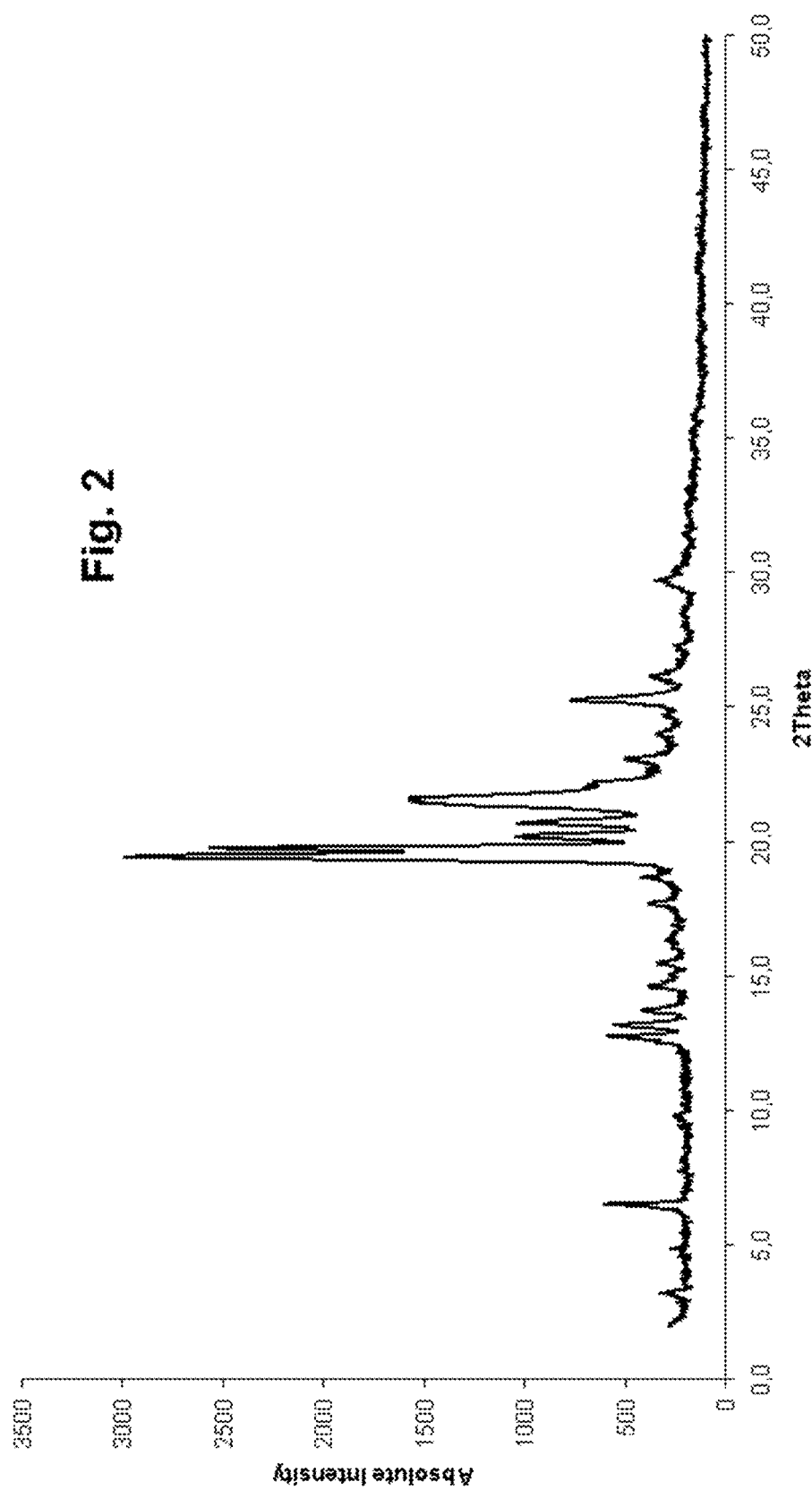
FIG. 2 illustrates x-ray spectra for crystalline (2S)-DOTAP chloride.
Figure 3:
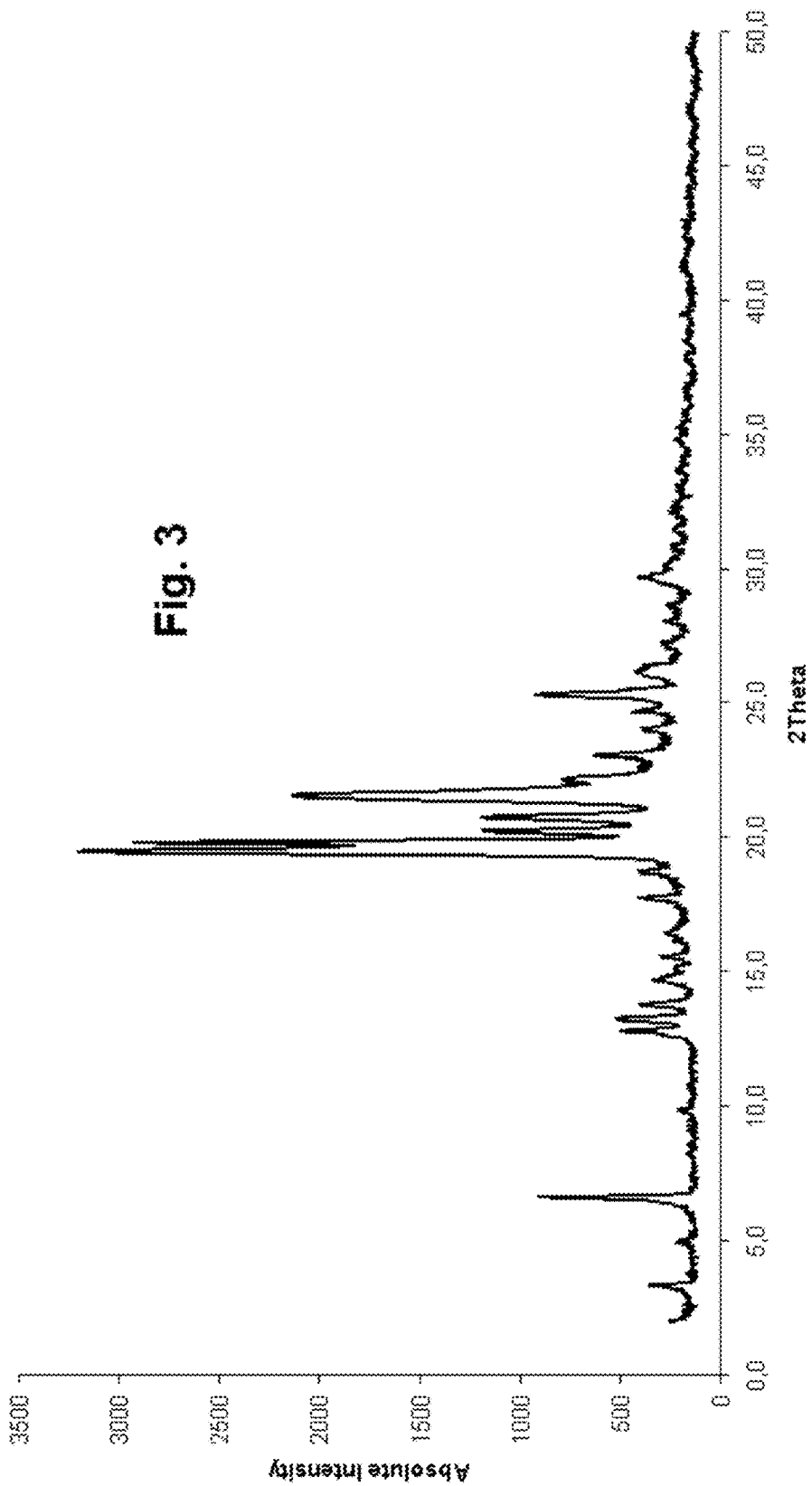
FIG. 3 illustrates x-ray spectra for crystalline (2R)-DOTAP chloride.

Examples of spectra are shown in FIG. 1, FIG. 2 and FIG. 3.

Figure 4:
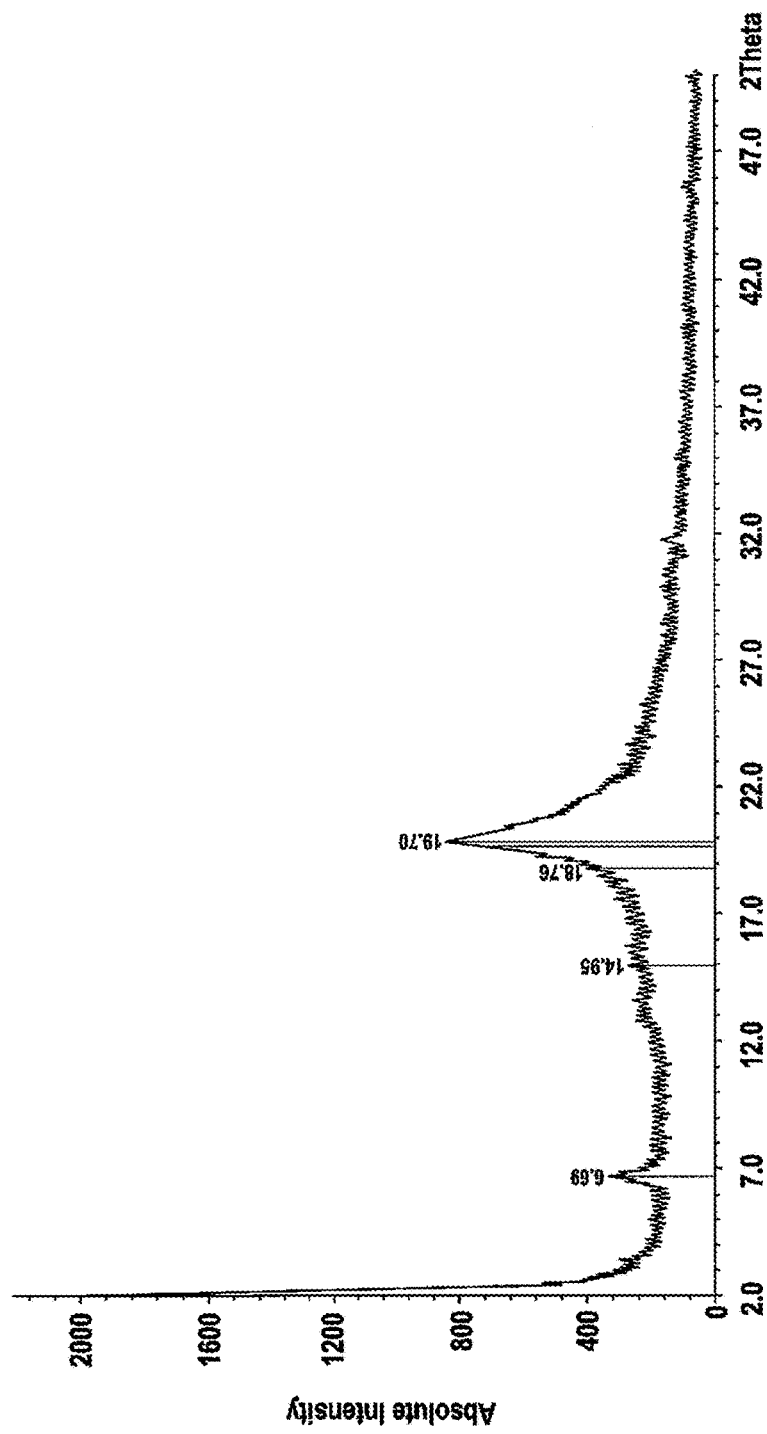
FIG. 4 illustrates x-ray spectra for amorphous (2R,S)-DOTAP chloride.
Figure 5:
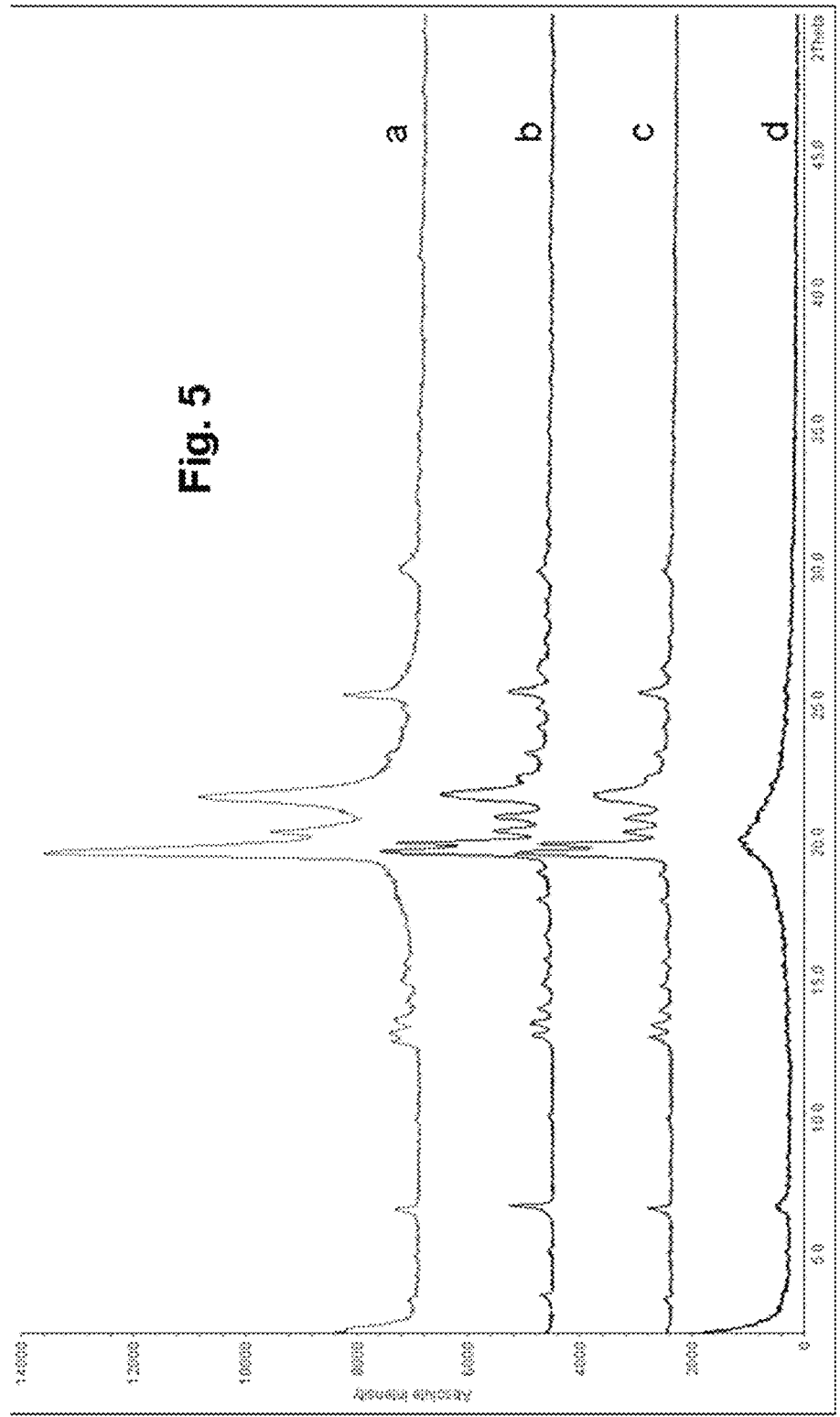
FIG. 5 illustrates x-ray spectra for crystalline (2R,S)-DOTAP chloride (a), crystalline (2R)-DOTAP chloride (b) and crystalline (2S)-DOTAP chloride (c) in comparison to a commercially available sample of (2R,S)-DOTAP chloride (Avanti Polar Lipids) (d)

For comparison, a spectrum of a commercially available, amorphous sample is shown in FIG. 4 (amorphous). FIG. 5 shows the comparison of the x-ray spectra for crystalline (2R,S)-DOTAP chloride (a), crystalline (2R)-DOTAP chloride (b) and crystalline (2S)-DOTAP chloride (c) in comparison to a commercially available sample of (2R,S)-DOTAP chloride (Avanti Polar Lipids) (d).

Table 2 lists selected 2 theta values for the various crystal modifications of racemic and enantiomerically pure DOTAP chlorides:

TABLE 2

| Type | | Selected 2 theta values |
| --- | --- | --- |
| (2R,S)-DOTAP | racemic | 12.6, 19.5, 20.2, 21.5 and 25.2 |
| (2S)-DOTAP | enantiomerically pure | 12.8, 19.5, 19.8, 20.2, and 21.6 |
| (2R)-DOTAP | enantiomerically pure | 12.8, 19.5, 19.8, 20.3, and 21.6 |

Characterization Example 3

Melting Point and Melting Enthalpy

The melting point and melting enthalpy of crystalline DOTAP chlorides is determined by differential scanning calorimetry (DSC) (30-350° C., 5.0° C./min, $N_2$ 80 ml/min).

The resulting melting points and melting enthalpies for racemic (2R,S)- and enantiomerically pure (2R)-resp. (2S)-DOTAP chlorides are listed in Table 3.

TABLE 3

| Type | | melting point | | melting enthalpy |
| --- | --- | --- | --- | --- |
| | | onset | peak | |
| (2R,S)-DOTAP | racemic | 161.0° C. | 183.5° C. | −143.7 J/g |
| (2R)-DOTAP | enantiomerically pure | 160.1° C. | 183.6° C. | −155.4 J/g |
| (2S)-DOTAP | enantiomerically pure | 159.2° C. | 184.7° C. | −158.4 J/g |

Characterization Example 4

Phase Transition Temperatures and Enthalpies

The phase transition temperatures and enthalpy of crystalline DOTAP chlorides are determined by differential scanning calorimetry (DSC) (30-350° C., 5.0° C./min, $N_2$ 80 ml/min).

In addition to the melting points (see Characterization Example 3) several transition points to crystalline resp. liquid-crystalline phases are observed.

The corresponding phase transition temperatures and enthalpies for racemic (2R,S)- and enantiomerically pure (2R)-resp. (2S)-DOTAP chlorides are listed in Table 4.

TABLE 4

| type | | (2R,S)-DOTAP racemic | (2R)-DOTAP enantiomerically pure | (2S)-DOTAP enantiomerically pure |
| --- | --- | --- | --- | --- |
| $1^{st}$ transition | onset | 49.8° C. | 40.9° C. | 41.0° C. |
| | peak | 57.4° C. | 42.7° C. | 43.0° C. |
| | enthalpy | −58.2 J/g | −14.1 J/g | −13.5 J/g |
| $2^{nd}$ transition | onset | 64.7° C. | 52.4° C. | 51.6° C. |
| | peak | 66.2° C. | 60.7° C. | 60.3° C. |
| | enthalpy | −25.0 J/g | −38.0 J/g | −37.0 J/g |
| 3rd transition | onset | — | 81.9° C. | 81.6° C. |
| | peak | — | 84.0° C. | 83.8° C. |
| | enthalpy | — | −33.9 J/g | −33.1 J/g |

Figure 6:
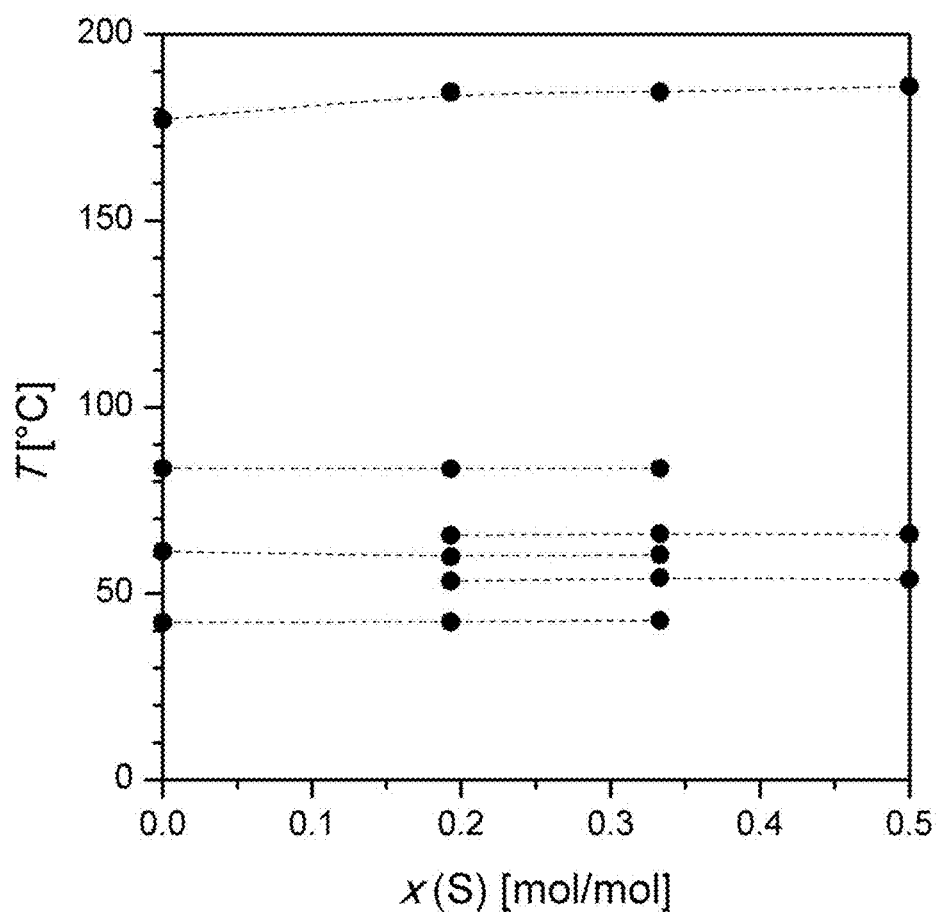
FIG. 6 illustrates the phase transition temperatures and melting points of pure crystalline (2R,S)-DOTAP chloride and pure crystalline (2R)-DOTAP chloride as well as two mixtures of both crystalline forms.

When the DSC experiment is performed on mixtures of pure crystalline (2R,S)-DOTAP chloride and pure crystalline (2R)-DOTAP chloride all phase transition temperatures of both, the racemate and the enantiomer, are observed. FIG. 6 illustrates the phase transition temperatures and melting points of pure crystalline (2R,S)-DOTAP chloride and pure crystalline (2R)-DOTAP chloride as well as mixtures of both crystalline forms in the ratio of 100:50 and 63:100. These ratios are corresponding to a content of 33.3 mol % resp. 19.3 mol % of (2S)-DOTAP chloride in the mixtures.

Conclusion:

The crystal modifications of crystalline enantiomerically pure DOTAP chloride and crystalline racemic DOTAP chloride are distinct.

Characterization Example 5

Water Absorption in Dependence on Relative Humidity

The water absorption of DOTAP chloride is determined by Dynamic Vapor Sorption (DVS) using a Projekt Messtechnik SPS 11-100n water vapour sorption analyzer. The samples are placed in aluminium crucibles on top of a microbalance and are allowed to equilibrate at 25° C. and 0% r.h. (relative humidity) over night before exposing them to two humidification/drying cycles at 25° C. with a scanning rate of Δ r.h.=5% $h^{-1}$ and 'isohumid' equilibration periods at the extreme values.

Samples of crystalline (2R,S)-DOTAP chloride, crystalline (2R)-DOTAP chloride, amorphous (2R,S)-DOTAP chloride and amorphous (2R)-DOTAP chloride are investigated.

Figure 7:
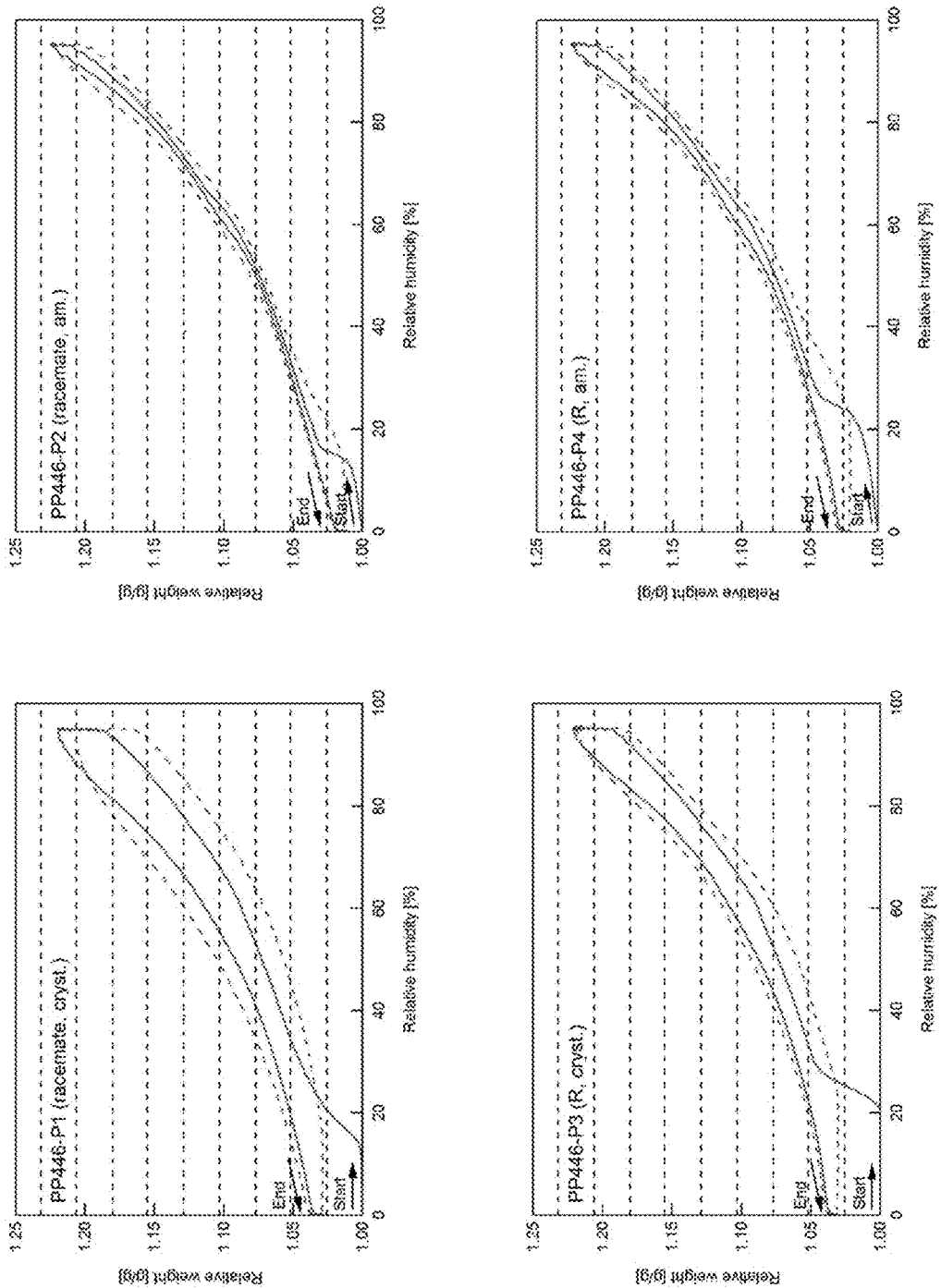
FIG. 7 illustrates the DVS curves for (2R,S)-DOTAP chloride (top) and (2R)-DOTAP chloride (bottom): amorphous forms: diagrams on the right; crystalline forms (diagrams on the left) (see Characterization Example 5).

Results:

The comparison of the DVS curves (see FIG. 7: first cycle solid line, second cycle dashed line) points out characteristic differences between the crystalline and amorphous samples: The crystalline samples (left diagrams of FIG. 7) exhibit a stable weight at low r.h., whereas the weight of the amorphous samples (right diagrams of FIG. 7) increase already right above 0% r.h. In addition, for the samples that had been crystalline at the beginning, a significantly larger hysteresis is observed in both cycles. A difference can also be observed between the racemic (top diagrams of FIG. 7) and the enantiomerically pure (bottom diagrams of FIG. 7) samples: The racemic samples exhibit a sharp increase in water content at ca. 10-15% r.h., whereas the isomerically pure samples exhibit this step at ca. 20-25% r.h.

Comparative Example 1

In the herein reproduced experiment of Feigner et al., all experimental conditions have been chosen to stay in close accordance with U.S. Pat. No. 5,264,618 (Feigner et al.), Example 5, column 27, lines 15 to 47.

31.5 g of oleoylchloride (FLUKA 07331AH) dissolved in 125 ml chloroform was added dropwise at 4° C. under cooling over a period of 1½ hour to 5.0 g of 3-(dimethylamino)-1,2-propanediol, dissolved in 37.5 ml chloroform and 25 ml of pyridine. The yellow solution was stirred overnight. Then 125 ml of cold water and 125 ml diethylether was added. The organic phase was washed twice with 100 ml of 0.5N HCL and also twice with 100 ml 0.5N sodium bicarbonate solution. 39 g anhydrous sodium sulfate was added and the so obtained suspension was filtrated and washed with 100 ml chloroform. The filtrate was then concentrated under reduced pressure at 40° C. 40.1 g of a brown liquid (SM-0318-A) having a (2R,S)-DODAP content of 24.3% w/w measured by HPLC resulted. A further drying under reduced pressure at 60° C. resulted in a reduction of weight to 31.2 g.

31.0 g of this material was purified by silicic acid column chromatography as follows:

Silica gel: 129 g (the amount of silica gel was calculated relative to the amount (2R,S)-DODAP) Merck 60 F 63-200 um Column: diameter 4 cm, height 60 cm Flow: about 8 ml/min As mobile phase first 1,500 ml methylene chloride (fractions 1-27), then 1,000 ml methylene chloride/methanol 95:5 (fractions 28-47) and finally 1,000 ml methanol was used. Fractions were collected and combined according to their TLC analysis. So fractions 4-33 were concentrated together under reduced pressure. 10.8 g of a brown oil (SM-0318-B) having a (2R,S)-DODAP content of 65.6% w/w measured by HPLC resulted. And fractions 34-42 resulted in 12.6 g of a brown oil (SM 0318-D) having a (2R,S)-DODAP content of 54.2% w/w measured by HPLC. 10.4 g Methylene chloride was added to 9.6 g of the compound obtained out of the fractions 4-33 (SM-0318-B) in a high pressure glass tube. The glass tube was then closed and the brownish solution was heated over night at 50° C. to form an emulsion. Then the tube was opened and residual methylene chloride was removed by evaporation. 8.0 g of a yellow wax (SM-0318-E) having a (2R,S)-DOTAP chloride content of 65.0% w/w and 1.3% w/w (2R,S)-DODAP both measured by HPLC resulted. 14.0 g acetonitrile was added to this wax (SM-0318-E). The so obtained emulsion was transferred with 80 ml acetonitrile (to obtain a ratio solid to solvent of about 1:12) into a flask and cooled down to 20° C. No crystallisation could be observed. At 20° C. a solidified honey like yellow-brownish material resulted which even when only slightly warming it up tended to become a sticky viscous brownish material.

Conclusion

The data demonstrate that 1,2-dioleoyl-3-propyltrimethylammonium chloride ((2R,S)-DOTAP chloride) prepared according to the above procedure, which is in accordance with U.S. Pat. No. 5,264,618 (Feigner et al), Example 5, column 27, lines 15 to 47 cannot be obtained in a crystalline form.

Comparative Example 2

A further reproduction of the experiment of Feigner et al., was prepared confirming the same finding as above.

All experimental conditions have been chosen to stay as close as possible to the conditions for the preparation/isolation of (2R,S)-DOTAP chloride as disclosed in U.S. Pat. No. 5,264,618 (Feigner et al) Example 5, column 27, lines 15 to 47.

In this experiment, special emphasis has been set on the scale of reactants, the use of anhydrous pyridine, the methylation time and the temperature of the tube.

Within U.S. Pat. No. 5,264,618 (Feigner et al) Example 5 no valid data on the used raw material could be found. For the rework oleoylchloride from SIGMA-ALDRICH (Art. Nr. 367850, Lot. 07331AH) and 3-(dimethylamino)-1,2-propanediol from TCI (Art. Nr. D2072, Lot. FGC01 EF) were used. Diethylether (Art. No. 8.22270.1000, Lot. No. K33237470), sodium sulfate (Art. No. 8.22286.5000, Lot. No. TA603386), sea sand (Art. No. 1.07711.5000, Lot. No. TA1417811), silica gel 60 F 63-200 µm (Art. No. 1.07734.9025, Lot. No. TA1570234) and acetonitrile (Art. No. 1.15500.1000, Lot. No. K38172000) all were from Merck KGaA. Chloroform (Art. No. 34854, Lot. No. 8178C) and pyridine over molecular sieve, H2O≤0.005% (Art. No. , 82704, Lot. No. 1166921) were from Fluka.

5.0 g of 3-(dimethylamino)-1,2-propanediol was dissolved at room temperature in 25 ml anhydrous pyridine and 37.5 ml freshly distilled chloroform. The solution was cooled down to 4° C. 31.5 g of Oleoylchloride was dissolved in 125 ml distilled chloroform. The oleoylchloride solution was added dropwise to the cold 3-(dimethylamino)-1,2-propanediol solution over a period of one hour. The yellow solution was stirred overnight. Then 125 ml cold water and 125 ml diethylether were added. The organic phase was washed twice with 100 ml HCl 0.5N and then also twice with 100 ml sodium bicarbonate solution 0.5N. Then 39 g anhydrous sodium sulfate were added. The so obtained suspension was filtrated and the residual solid was washed with 20 ml chloroform. The filtrate was then concentrated under reduced pressure. 31.5 g of a brown liquid (SM 0364 A) having a 1,2-dioleoyl-3-dimethylammonium propane (DODAP) content of 62.2% w/w measured by HPLC resulted.

A silica gel column was prepared as follows:

Column: diameter 4 cm, height 60 cm

Silica gel: 200 g silica gel and 42.6 g sea sand (calculated relative to the amount of DODAP)

Flow: about 7 ml/min 15 g of the material prepared above (SM 0364 A) were added dropwise onto the silica gel column and rinsed with 50 ml chloroform. The column was first eluted with 1,000 ml chloroform, then with 1,000 ml chloroform/methanol 95/5, then with 1,250 ml chloroform/methanol 90/10 and finally with 2,500 ml methanol. Fractions were collected and combined according to their thin layer chromatography analysis on silica gel plates (Merck 60 F254), developed with chloroform/acetone/methanol/acetic acid/water 50/15/5/5/2 by volume, detection by iodine. After concentrating under reduced pressure combined fractions 11-17 resulted in 4.88 g (SM 0364 B) having a DODAP content of 73.2% w/w, fractions 18-27 resulted in 7.24 g (SM 0364 C) having a DODAP content of 68.2% w/w and fractions 28-31 resulted in 1.9 g (SM 0364 D) having a DODAP content of 40.4% w/w all measured by HPLC. In total a mass balance of 93.5% resulted.

1.0 g of the compound obtained out of the purest fractions 11-17 (SM-0364-B) was added in a high pressurizable, heavy-wall borosilicate glass tube (Sigma Aldrich Z181072-1 EA). Then 10 ml methyl chloride were condensed into the glass tube. The glass tube was then tightly closed and kept for 72 hours at 70° C. Then the tube was cooled down to 0° C., opened and residual methyl chloride was removed by evaporation. This resulted in 1.11 g of a yellow-brownish wax (SM 0364 E) having a (2R,S)-DOTAP chloride content of 69.3% w/w and showing a DODAP content of 1.8% w/w and an oleic acid content of 2.7% w/w (all measured by HPLC).

To 1.08 g of the compound obtained as described above (SM 0364 E) 10 ml acetonitrile were added and heated to 50° C. The so obtained emulsion was cooled down to −20° C. No crystallisation could be observed. At −20° C. a yellow-brownish wax resulted.

Conclusion:

As shown above when reworking the closest embodiment (s) of U.S. Pat. No. 5,264,618 (Feigner et al) only amorphous (2R,S)-DOTAP chloride could be obtained.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Crystalline 2R,S)-, (2S)- or (2R)-DOTAP chloride, which crystalline (2R,S)-DOTAP chloride has one of the following characteristics:
   2 theta values comprising at least values of about 12.6, about 19.5, about 20.2, about 21.5 and about 25.2; or
   2 theta values comprising at least values of about 6.5, about 12.6, about 13.4, about 19.5, about 20.2, about 21.5, about 25.2 and about 29.8;
   or
   which crystalline (2S)-DOTAP chloride has one of the following characteristics:
   2 theta values comprising at least values of about 12.8, about 19.5, about 19.8, about 20.2, and about 21.6; or
   2 theta values comprising at least values of about 6.5, about 12.8, about 19.5, about 19.8, about 20.2, about 20.7, about 21.6 and about 25.3;
   or
   which crystalline (2R)-DOTAP chloride has one of the following characteristics:
   2 theta values comprising at least values of about 12.8, about 19.5, about 19.8, about 20.3, and about 21.6; or
   2 theta values comprising at least values of about 6.6, about 12.8, about 19.5, about 19.8, about 20.3, about 20.8, about 21.6 and about 25.3.

2. Crystalline (2R,S)-, (2S)- or (2R)-DOTAP chloride, which has a stability of higher than 99% by weight and Area-% higher than 99% determined by HPLC when stored at 25° C. for 36 months or at 40° C. for 12 months.

3. Crystalline (2R,S)-, (2S)- or (2R)-DOTAP chloride, which has a chemical purity of at least about 95% determined by HPLC.

4. Crystalline (2R,S)-, (2S)- or (2R)-DOTAP chloride according to claim 1, which has a melting point of higher than 160° C. and a melting enthalpy of more than −130 J/g.

5. A pharmaceutical composition comprising crystalline (2R,S)-, (2S)- or (2R)-DOTAP chloride according to claim 1 and a pharmaceutically acceptable carrier.

6. A pharmaceutical composition according to claim 5, further comprising one or more peptides, nucleotides, antigenes, cytostatic agents, liposomes, lipoplexes, nanoparticles or microemulsions, or a mixture thereof.

7. A process for preparing a crystalline form of (2R,S)-, (2S)- or (2R)-DOTAP chloride,
   which crystalline (2R,S)-DOTAP chloride has one of the following characteristics:
   2 theta values comprising at least values of about 12.6, about 19.5, about 20.2, about 21.5 and about 25.2; or
   2 theta values comprising at least values of about 6.5, about 12.6, about 13.4, about 19.5, about 20.2, about 21.5, about 25.2 and about 29.8;
   or
   which crystalline (2S)-DOTAP chloride has one of the following characteristics:
   2 theta values comprising at least values of about 12.8, about 19.5, about 19.8, about 20.2, and about 21.6; or
   2 theta values comprising at least values of about 6.5, about 12.8, about 19.5, about 19.8, about 20.2, about 20.7, about 21.6 and about 25.3;
   or
   which crystalline (2R)-DOTAP chloride has one of the following characteristics:
   2 theta values comprising at least values of about 12.8, about 19.5, about 19.8, about 20.3, and about 21.6; or
   2 theta values comprising at least values of about 6.6, about 12.8, about 19.5, about 19.8, about 20.3, about 20.8, about 21.6 and about 25.3;
   comprising crystallizing (2R,S)-, (2S)- or (2R)-DOTAP chloride from one or more aprotic solvents selected from ether, ketone or ester aprotic solvents, wherein the crystallizing takes place by slow cooling at a rate of 0.001° C. to 0.05° C. per minute for 10 to 50 hours to a temperature of −12° C. or less.

8. A process according to claim 7, wherein the one or more aprotic solvents are in mixture with one or more protic solvents.

9. A process according to claim 7, wherein the crystallizing takes place under an inert atmosphere.

10. A process according to claim 7, where crystallization is carried out directly from a reaction solution without prior purification, which reaction solution is from a process of preparing (2R,S)-, (2S)- or (2R)-DOTAP chloride.

11. A process according to claim 7, which further comprises a recrystallization of crystalline (2R,S)-, (2S)- or (2R)-DOTAP chloride.

12. Crystalline (2R,S)-, (2S)- or (2R)-DOTAP chloride obtained by a process according to claim 7.

13. A method of transfecting a cell, comprising administering to said cell a crystalline (2R,S)-, (2S)- or (2R)-DOTAP chloride according to claim 1.

14. A process according to claim 7, wherein the solvent comprises the aprotic solvent acetone and the protic solvent 2-propanol.

15. A process according to claim 7, wherein the solvent comprises the aprotic solvent acetone and the protic solvent 2-propanol and the process further comprises recrystallizing the crystalline (2R,S)-, (2S)- or (2R)-DOTAP chloride wherein the recrystallizing comprises dissolving the crystalline (2R,S)-, (2S)- or (2R)-DOTAP chloride in mixture of the aprotic solvent acetone and the protic solvent 2-propanol and slowly cooling at a rate of 0.001° C. to 0.05° C. per minute for 10 to 50 hours to a temperature of −12° C. or less.

* * * * *